United States Patent [19]
Frisch et al.

[11] Patent Number: 5,512,534
[45] Date of Patent: Apr. 30, 1996

[54] CROP-PROTECTION FORMULATIONS

[75] Inventors: Gerhard Frisch, Wehrheim/Taunus; Thomas Maier, Frankfurt am Main, both of Germany

[73] Assignee: Hoechst Aktiengesellschaft, Germany

[21] Appl. No.: 131,289

[22] Filed: Oct. 4, 1993

[30] Foreign Application Priority Data

Oct. 3, 1992 [DE] Germany .................. 42 33 309.1

[51] Int. Cl.$^6$ .................. A01N 57/12; C07F 9/09
[52] U.S. Cl. .................. 504/103; 504/116; 514/120; 514/129; 558/179; 558/186
[58] Field of Search .................. 558/179, 186; 514/120, 129; 504/103, 116

[56] References Cited

U.S. PATENT DOCUMENTS

| | | | |
|---|---|---|---|
| 3,056,744 | 10/1962 | Copes et al. | 558/186 X |
| 3,462,520 | 8/1969 | Nehmsmann et al. | 558/186 |
| 3,723,578 | 3/1973 | Eiseman, Jr. et al. | 558/186 X |
| 3,740,364 | 6/1973 | Schuler et al. | 558/179 X |
| 4,781,722 | 11/1988 | Kleiner et al. | 8/127.1 |

FOREIGN PATENT DOCUMENTS

| | | |
|---|---|---|
| 0281043 | 9/1988 | European Pat. Off. . |
| 1258976 | 3/1960 | France . |
| 4-69389 | 7/1992 | Japan . |
| 2183653 | 6/1987 | United Kingdom . |

OTHER PUBLICATIONS

*Chemical Abstracts* 1992, 117(13):131382; K. Yamaki, JP04069389, published Mar. 4, 1992.
Database WPI, Derwent Publications Ltd., London, GB; AN 72–60932T(38) & JP-A-47 037008 (Ishihara Sangyo Kaisha) 1972.

*Primary Examiner*—Johann Richter
*Assistant Examiner*—Michael G. Ambrose
*Attorney, Agent, or Firm*—Connolly & Hutz

[57] ABSTRACT

The present invention relates to compounds of the formula I

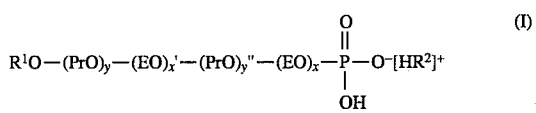

in which $R^1$ is hydrogen,
a substituted or unsubstituted aliphatic radical having up to 30 carbon atoms,
a substituted or unsubstituted alicyclic radical having up to 30 carbon atoms,
a substituted or unsubstituted aromatic radical having up to 24 carbon atoms or
a substituted or unsubstituted heteroaromatic radical having up to 20 carbon atoms, $R^2$ is an amino acid, $x'=0-80$, $y'=0-50$, $x''=0-80$ and $y''=0-50$, with at least one of the variables $x'$, $y'$, $x''$ and $y''$ being greater than 0. The compounds of the formula I are prepared by reacting the corresponding dihydrogen phosphate with the respective amino acid or salt thereof. The compounds according to the invention can be employed, for example, as surfactants for emulsifying organic solvents in water.

10 Claims, No Drawings

CROP-PROTECTION FORMULATIONS

For the emulsification of organic solvents it has been known to employ, inter alia, surfactants which contain one or more ethylene oxide groups (EO) and/or propylene oxide groups (PRO). Examples of such surfactants are n-$(C_1-C_{18})$-alkylphenols which contain 1–50 EO groups and may be mono-, di- or trisubstituted (e.g. ®Arkopal or the ®Sapogenat series; Hoe S 2435 (Hoechst AG))- The phenol radical may also be mono-, di- or triaryl-substituted and likewise contain 1–50 EO groups (e.g. Hoe 3474 (Hoechst AG); ®Soprophor BSU, the ®Soprophor DS series (Rhone Poulenc) or surfactants such as are described in, for example, EP-A-0 062 181, EP-A-0 297 207, EP-A-0 196 463 and EP-A-0 107 009). Other such surfactants are primary, secondary and tertiary alcohols containing one or more EO and/or PrO groups, which have a chain length of $C_6-C_{24}$ (branched or unbranched) such as, for example, oleyl alcohols, stearyl alcohols, tallow fatty alcohols, coconut fatty alcohols, isotridecyl alcohols, Guerbet alcohols (e.g. ®Genapol (Hoechst AG) grades C, O, S, T, X, ZL, ZDM and SE). Natural oils such as castor oil, which may be ethoxylated and/or propoxylated (e.g. the ®Emulsogen series (Hoechst AG)), are also suitable for emulsifying organic solvents in water, with the solvents possibly also containing substances which may be active in agrochemicals, pharmaceuticals and/or veterinary medicine.

Block polymers based on EO/PrO can also be utilized for their good emulsification properties. Examples which may be mentioned are: Hoe S 3510, Hoe S 1816, Hoechst AG, and the ®pluriol and ®pluronic series from BASF;

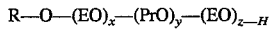

where
R is $(C_1-C_{10})$-alkyl or H
x=4–80
y=4–50
z=4–80

The abovementioned surfactants are nonionic surfactants whose properties can be modified by subjecting the free terminal OH group(s) to, for example, sulfation or phosphation. A variety of known methods are suitable for the phosphation, for example wet-phosphation with $H_3PO_4$, phosphation with polyphosphoric acid or reaction with $P_2O_5$. The particular variants of each method and the amount of phosphorus compound which are employed determine whether mono-, di- or triesters are obtained. Of particular interest in the present case are the mono- and diesters, specifically the monoesters, which are commercially available as such or in a neutralized form, for example as the triethanolamine or potassium salt (e.g. ®Soprophor 3 D 33, ®Soprophor FL (Rhone Poulenc); Hoe S 3475, Hoe S 3618, Hoe S 3775 (Hoechst AG)).

T. Suzuki et al. describe a process (J. Colloid and Interfac. Sci. 129, No. 2, [1989], 491 ff.) in which they subject monohexyldecyl alcohol to phosphation to give a monohexadecyl phosphate which they react with arginine to form monoarginine hexadecyl phosphate. The authors use this compound, in the form of liquid crystals (LC formation), to stabilize O/W emulsions. The gel-like emulsions which this forms are used for cosmetics.

It has now been found, surprisingly, that if the surfactants described above, which are ethoxylated and/or propoxylated and have then been phosphated, are reacted with amino acids, preferably basic amino acids or salts thereof, for example tryptophan, arginine, lysine, histidine, 2,4-diaminobutyric acid hydrochloride and ornithine monohydrochloride, the surfactants obtained exhibit liquid-crystalline properties.

The invention therefore relates to compounds of the formula I

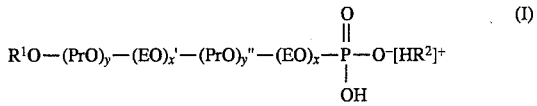

in which
$R^1$ is hydrogen,
a substituted or unsubstituted aliphatic radical having up to 30 carbon atoms,
a substituted or unsubstituted alicyclic radical having up to 30 carbon atoms,
a substituted or unsubstituted aromatic radical having up to 24 carbon atoms or
a substituted or unsubstituted heteroaromatic radical having up to 20 carbon atoms, $R^2$ is an amino acid,
x'=0–80,
y'=0–50,
x"=0–80 and
y"=0–50,
with at least one of the variables x', y', x" and y" being greater than 0.

Preferred compounds of the formula I are those in which
$R^1$ is hydrogen,
$(C_1-C_{24})$-alkyl which may be substituted and/or unsaturated,
$(C_1-C_{24})$-alkanoyl which may be substituted and/or unsaturated, or
$(C_6-C_{12})$-aryl which may be substituted and $R_2$, x', y', x" and y" are as defined above, and compounds of the formula I which are particularly preferred are those in which $R^1$ is hydrogen,
$(C_1-C_{24})$-alkyl, ricinoleyl or phenyl which is substituted with 1, 2 or 3 identical or different radicals from the group comprising $(C_1-C_{16})$-alkyl and ($C_6-C_{12}$)-aryl, $R^2$ is a basic amino acid and x', y', x" and y" are as defined above.

Compounds of the formula I which are very particularly preferred are those in which
$R^1$ is hydrogen,
$(C_1-C_{24})$-alkyl, ricinoleyl or
mono-, di- or tri- $(C_1-C_{16})$-alkylphenyl or
mono-, di- or tri- $(C_6-C_{12})$-arylphenyl, and $R^2$, x', y', x" and y" are as defined above. If x" is 0, then x' is preferably greater than 0.

Alkyl is preferably unbranched. The same applies to radicals derived from alkyl.

Preferred meanings of aryl are phenyl, naphthyl or biphenyl, or styryl as a substituted aryl. The amino acids which are particularly preferred are the basic amino acids, such as lysine, δ-hydroxylysine, arginine, tryptophan, histidine, ornithine or 2,4-diaminobutyric acid, or homologs thereof. Where the amino acids contain centers of chirality, then they may be present as the optically pure compounds in the L- or the D-form, preferably the L-form, or else in the form of mixtures of stereoisomers, such as racemates.

The compounds of the formula I can be prepared by, for example, reacting the corresponding dihydrogen phosphates with the respective amino acids, for example in $C_1$–$C_4$-alcohols such as methanol, or a ketone such as acetone. They are then taken up in water and maintained at 70°–75° C. for 120–150 min with gentle stirring. Cooling is followed by the precipitation of a wax-like product which was again taken up in methanol or acetone and then filtered (a procedure repeated 2 times). The products which result after removing the methanol or acetone by evaporation are wax-like and may be brownish to yellowish depending on the amino acid employed, and they can be employed, for example, in the emulsions or suspoemulsions described below.

The products concerned are in point of fact those which surprisingly exhibit liquid-crystalline properties. This was not foreseeable, since the unphosphated and the phosphated products, whether alone or in the form of, for example, their ammonium, potassium or triethanolamine compounds neither exhibit this effect nor show any indication that they do so. Their liquid-crystalline behavior is evident, for example, in 1% strength solution in, for example, aromatic solvents such as xylene, toluene or Solvesso®200 in 2:1 dilution with water, when the solution is viewed through a microscope in polarized light. It is possible to make out clearly the 4-leaved clover shape (spherulites) of the liquid crystals (laminar phase). This is evidence of the existence of liquid crystals.

These liquid-crystalline products can be used, for example, as surfactants for emulsifying organic solvents, preferably aromatic solvents, in water.

These organic solvents can have been used to dissolve biologically active substances, preferably agrochemical, pharmaceutical or veterinary active substances, to which from 0.1–10%, but preferably from 0.5–5%, of the surfactants described here are added. The proportion of the organic phase may be from 0.1 to 85%, but is preferably from 1–60%.

The active substances are selected from the series comprising herbicides, insecticides, fungicides, acaricides, nematicides, pheromones and repellents, preferably from the series of herbicides and insecticides. The formulations may contain at least one safener.

Suitable herbicides are in particular foliar herbicides which realize their biological potential primarily or to a greater extent in dissolved form, but which are intended to be employed as solid formulations. Examples of suitable herbicidal active substances are phenoxy-phenoxy- or heteroaryloxyphenoxypropionic acid alkyl esters such as methyl α-4-(2'4'-dichlorophenoxy)phenoxypropionate [common name: diclofopmethyl] (A), ethyl 2-[4-(6-chloro-2-benzthiazolyloxy)phenoxy]-propionate (B) or ethyl 2-[4-(6-chloro-2-benzoxazolyloxy)phenoxy]-propionate (common name: fenoxaprop-P ethyl) (C), dinitroaniline compounds such as 2,6-dinitro4-trifluoromethyl-N,N-dipropylaniline [common name: trifluralin] (D) or 2,6-dinitro-4-isopropyl-N,N-dipropylaniline [common name: isopropalin] (E), hydroxybenzonitrile derivatives such as 2,6-dibromo-4-hydroxybenzonitrile octanoate (F) and dinitrophenol compounds such as 2-sec-butyl-4,6-dinitrophenol [common name: dinoterb] (G).

Examples of suitable safeners are the compounds described in EP-A-86 750, EP-A-191 736, EP-A-346 620, EP-A-333 131, EP-A-269 806, EP-A-159 290, DE-A-2 546 845, PCT/EP-90/02020 and PCT/EP-90/01966.

Examples of suitable insecticides are 1,4,5,6,7,7-hexachloro-8,9,10-trinorborn-5-en-2,3-ylene dimethyl sulfite [common name: endosulfan], 2-(1-methyl-n-propyl)-4,6dinitrophenyl 2-methylcrotonate [common name: binapacryl], phosphoric acid esters such as O,O-diethyl O-1-phenyl-1H-1,2,4-triazol-3-yl phosphorothioate [common name: triazophos] or pyrethroids such as (S)-α-cyano-3phenoxybenzyl (1R,3R)-3-(2,2-dibromovinyl)-2,2-dimethylcyclopropanecarboxylate [common name: deltamethrin] or 4-ethoxyphenyl-[3-(4-fluoro-3-phenoxyphenyl)propyl]dimethylsilane (silafluofen).

An example of a suitable fungicide is ethyl 2-diethoxythiophosphoryloxy-5-methyl-pyrazolo [1,5-a]pyrimidine-6carboxylate [common name: pyrazophos], suitable pheromones are the compounds (E)-8-(E)- 10-dodecadienol and (Z)-7,8-epoxy-2-methyloctadecane, and a suitable repellent is dimethyl phthalate.

The herbicides mentioned above (with the exception of compound (B)), the insecticides and the repellent are known from H. Martin, Pesticide Manual, 6th edition, 1979. The herbicides (B) and (C) are described in DE-A2 640 730 and the two pheromones in M. Beroza, Chem. Controlling Insect Behavior, Academic Press, N.Y. 1970.

The term organic phase as used here refers to the surfactant, the solvent and the substance(s) dissolved in it. The proportion of active substance dissolved in the solvent depends on the particular active substance chosen and its solubility in the particular organic solvent selected.

Suitable solvents are all those organic solvents which are not miscible with water, but preferably ketones such as isophorone, cyclohexanone, acetophenone, methyl benzyl ketone and cyclopentanone, or aromatic hydrocarbons, preferably those based on phenyl and/or naphthyl structures, which may be substituted from 1–5 times, preferably by alkyl, or else phthalic acid diesters. In addition to the surfactants described above being used alone, they may also be mixed with one another in any desired ratio; in the case of 2 surfactants, a ratio of from 50:1 to 1:50 is preferred. However, combinations can also be formed by mixing together more than 2 of these amino acid phosphate surfactants.

Similarly, 1 or more of these amino acid phosphates may be mixed with other commercial surfactants of ionic or nonionic type, the aim of such a combination being to obtain even better emulsification properties in the specific case where this is required. Many of these surfactants are described in "McCutchean's Emulsifier & Detergents", National and International Edition 1988 (McCutchean's Division, Glen Rock, N.J. USA).

Additional dispersants which may be employed are preferably lignosulfonates, Na salts of dinaphthylmethanedisulfonic acids, the Na salt of a sulfonic acid from cresol, formaldehyde, sodium sulfite and oxynaphthalenesulfonic acid, the Na salt of a sulfonic acid from m-cresol, formaldehyde and sodium sulfite, condensation products of arylsulfonic acids and formaldehyde Na salts, triethanolamine salts of phosphorylated polystyrylphenylpolyethylene oxides, polyvinyl alcohol, calcium dodecylbenzenesulfonate, and alkylnaphthalenesulfonates of various alkyl chain length.

Additional emulsifiers which may be employed are nonionic, anionic or cationic surface-active substances, mixtures of nonionic with anionic components predominantly being employed. However, it is also possible to use combinations of nonionic with cationic surface-active agents. The emulsifiers which it is preferred to employ include calcium phenylsulfonate, ethoxylated nonylphenols, ethoxylated aliphatic alcohols, ethoxylated castor oil, fatty acid polyglycol esters, propylene glycol/ethylene glycol block polymers and mixtures thereof, and phosphorylated ethylene glycol/propylene glycol/ethylene glycol block polymers.

Due to their liquid-crystalline properties, these amino acid phosphates accumulate effectively at the interface between the oil droplets and the carrier phase—water—and therefore shield the water phase from the oil phase effectively. This is of particular importance when the substances dissolved in the oil phase are sensitive to hydrolysis. This can be demonstrated using heptenophos in EW formulation or a mixture of amidosulfuron with fenoxaprop-P ethyl as an SE formulation (suspoemulsion) as examples.

and in combination with Soprophor BSU (tristyrylphenol ethoxylate with about 18 EO).

LC 29382 is a product of tristyrylphenol with 18 EO, phosphated and condensed with arginine LC 29397 is a product of EO-PrO-EO (Hoe 3618), phosphated and condensed with arginine LC 29490 is a product of EO-PrO-EO (Hoe 3618), phosphated and condensed with tryptophan LC 29491 is a product of tristyrylphenol with 18 EO, phosphated and condensed with tryptophan Examples Tables A+B

| A | 1 | 2 | 3 | 4 | 5 | 6 | 7 | 8 | 9 | 10 | |
|---|---|---|---|---|---|---|---|---|---|---|---|
| Heptenophos | 25.1 | 25.1 | 25.1 | 25.1 | 25.1 | 25.1 | 25.1 | 25.1 | 25.1 | 25.1 | 25.1 |
| Solvesso 200 | 23.5 | 23.5 | 23.5 | 23.5 | 23.5 | 23.5 | 23.5 | 23.5 | 23.5 | 23.5 | 23.5 |
| LC 29382 | 1 | 2 | 3 | 4 | 5 | 6 | 7 | 1 | 7 | 0.1 | 0.5 |
| Soprophor FL | | | | | | | | 7 | 7 | | |
| Water to 100% | | | | | | | | | | | |
| Active ingredient content after 3 months | | | | | | | | | | | |
| RT | 24.8 | 23.7 | 22.9 | 23.1 | 23.0 | 24.6 | 23.5 | 23.2 | 23.2 | 25.0 | 25.0 |
| 40° C. | 21.5 | 20.5 | 20.0 | 18.0 | 18.5 | 17.5 | 17.0 | 18.0 | 19.5 | 22.0 | 23.0 |
| 50° C. | 16.5 | 15.5 | 12.5 | 12.0 | 11.5 | 9.5 | 9.0 | 9.5 | 6.5 | 12.8 | 17.1 |

| B | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Heptenphos | 25.1 | 25.1 | 25.1 | 25.1 | 25.1 | 25.1 | 25.1 | 25.1 | 25.1 | 25.1 | 25.1 | 25.1 | 25.1 | 25.1 |
| Solvesso 200 | 23.5 | 23.5 | 23.5 | 23.5 | 23.5 | 23.5 | 23.5 | 23.5 | 23.5 | 23.5 | 23.5 | 23.5 | 23.5 | 23.5 |
| LC 29397 | 1 | 2 | 3 | 4 | 5 | 6 | 7 | 1 | 7 | 0.1 | 0.5 | 1 | 2 | 3 |
| Soprophor FL | | | | | | | | 7 | 7 | | | 1 | 2 | 3 |
| Water to 100% | | | | | | | | | | | | | | |
| Active ingredient content after 3 months | | | | | | | | | | | | | | |
| RT | 24.3 | 23.5 | 23.6 | 23.5 | 23.9 | 23.8 | 23.7 | 13.4 | 23.8 | 25.0 | 25.0 | 24.5 | 25.0 | 25.0 |
| 40° C. | 21.9 | 21.6 | 21.1 | 21.1 | 20.7 | 20.8 | 20.8 | 18.5 | 17.7 | 22.5 | 23.0 | 20.0 | 17.0 | 17.0 |
| 50° C. | 17.0 | 16.9 | 16.1 | 15.3 | 15.3 | 15.4 | 14.7 | 9.3 | 9.2 | 18.5 | 17.0 | 16.5 | 16.5 | 16.5 |

Under normal conditions, heptenophos is degraded in an aqueous environment at room temperature (RT) within a matter of days. It is also apparent that only a little is required to have a markedly increased effect. Combinations with other surfactants tend to show an impairment of the storage properties. Another item of interest is the different behavior of LC 29382 and LC 29397 at relatively high concentrations.

The examples below are of suspoemulsions of amidosulfuron and fenoxaprop-P ethyl, combined, using different LCs. Here too the degradation of amidosulfuron in water can be markedly reduced, with LC both as the sole surfactant LC 29492 is a product of EO-PrO-EO (Hoe 3618), phosphated and condensed with lysine monohydrochloride LC 29493 is a product of tristyrylphenol with 18 EO, phosphated and condensed with lysine monohydrochloride

| C | 1 | 2 | 3 X | 4 X | 5 X | 6 | 7 XX | 8 | 9 | 10 |
|---|---|---|---|---|---|---|---|---|---|---|
| Org. phase with LC 29490 | 50 | | | 50 | | | | | | 50 |
| Org. phase with LC 29492 | | 50 | 50 | | | | | | 50 | |
| Org. phase with LC 29397 | | | | | 50 | 50 | 50 | 50 | | |
| Hoe 075032 | 13 | 13 | 13 | 13 | 13 | 13 | 13 | 13 | 13 | 13 |
| Proportion in dispersion | | | | | | | | | | |

-continued

| | C | | | | | | | | | |
|---|---|---|---|---|---|---|---|---|---|---|
| | 1 | 2 | 3 X | 4 X | 5 X | 6 | 7 XX | 8 | 9 | 10 |
| Water to 100% Analysis | | | | | | | | | | |
| Hoe 46360, freshly prepared | 5.7 | 5.66 | 5.62 | 5.25 | 5.62 | 5.81 | 4.9 | 6.28 | 6.42 | 6.02 |
| 3 months at 40° C. | 6.1 | 5.7 | 5.55 | 5.35 | 5.58 | 6.2 | 4.98 | 6.42 | 17.7 | |
| Hoe 075032, freshly prepared | 3.1 | 3.1 | 2.87 | 2.93 | 2.87 | 3.11 | 3.12 | 3.15 | 3.15 | 3.05 |
| 3 months at 40° C. | 1.95 | 2 | 1.92 | 1.95 | 1.93 | 20.4 | 1.5 | 2.10 | 2.13 | 1.98 |
| Hoe 070542, freshly prepared | / | / | / | / | / | / | / | 2.97 | 3.12 | 2.68 |
| Hoe 070542, 3 months 40° C. | / | / | / | / | / | / | / | 2.94 | 3.00 | 2.92 |

The formulations designated in Table C with an X contain ®Soprophor FL instead of ®Soprophor BSU, and the formulation designated with XX contains only ®Soprophor FL and no LC content, as is also evident from the markedly greater decrease after 3 months at 40° C. in the case of Hoe 075032.

The proportion of amidosulfuron ( Hoe 075032 ) in the dispersion is based on the following base formulation (30518):

| 25.3% of | amidosulfuron |
|---|---|
| 10.0% of | ®Sokolan CP 10 |
| 1.0% of | ®Darvan No. 3 |
| 2.0% of | ®Meranil A powder |
| 2.0% of | Defoamer SE 2 |
| 0.2% of | ®Rhodopol 23 |
| 0.1% of | ®Kobate C |
| 8.0% of | glycerol |
| 51.4% of | water |

The organic phase with fenoxaprop-P ethyl, on its own or, if required, with fenchlorazol e-ethyl, has the following composition; if fenchlorazol e-ethyl is employed, the corresponding weight % of Solvesso 150 is deducted. Likewise, the relevant LC proportion can be replaced by the other LC variants described, or they can be combined.

| 13.2% of | fenoxaprop-P ethyl |
|---|---|
| 10.0% of | rapeseed oil |
| 10.0% of | ®Soprophor BSU |
| 2.0% of | LC 29490 |
| 64.8% of | ®Solvesso 150 |

We claim:

1. A crop protection formulation, comprising:
   an organic phase, said organic phase comprising an organic solvent and, dissolved therein, a herbicide, an insecticide, a fungicide, an acaricide, a nematicide, pheromone, or a repellant, said organic phase being in the form of droplets,
   a carrier phase comprising water, and at the interface between the organic phase and the carrier phase, a liquid crystal of the formula I

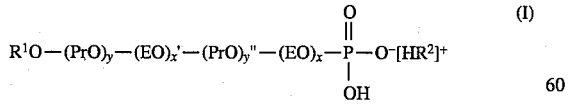

in which
   $R^1$ is hydrogen,
      a substituted or unsubstituted aliphatic radical having up to 30 carbon atoms,
      a substituted or unsubstituted alicyclic radical having up to 30 carbon atoms,
      a substituted or unsubstituted aromatic radical having up to 24 carbon atom or
      a substituted or unsubstituted heteroaromatic radical having up to 20 carbon
   $R^2$ is a basic amio acid or salt thereof capable of imparting liquid-crystal properties to said liquid crystal,
   x is 0 to 80,
   y is 0 to 50,
   x' is 0 to 80, and
   y" is 0 to 50,
   at least one of the variables x, y, x', and y" being greater than zero. EO represents an ethylene oxide group, and PrO represents a propylene oxide group.

2. A crop protection formulation according to claim 1, wherein said herbicide, insecticide, fungicide, acarcide, nematicide, pheromone, or repellent is subject to hydrolysis by said carrier phase but is protected therefrom by said liquid crystal.

3. A water-based crop-protection formulation composition, comprising:
   water; an organic solvent; at least one of the following active substances: a herbicide, an insecticide, a fungicide, an acaricide, a nematicide, a pheromone, or a repellant; and a compound of the formula I

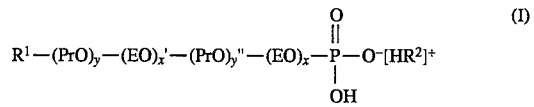

in which
   $R^1$ is hydrogen,
      a substituted or unsubstituted aliphatic radical having up to 30 carbon atoms,
      a substituted or unsubstituted alkanoyl radical having up to 30 carbon atoms,
      a substituted or unsubstituted alicyclic radical having up to 30 carbon atoms,
      a substituted or unsubstituted aromatic radical having up to 24 carbon atoms or
      a substituted or unsubstituted heteroaromatic radical having up to 20 carbon atoms,
   $R^2$ is an amino acid,
   x=0–80,
   y=0–50,
   x'=0–80 and
   y"=0–50,
   with at least one of the variables x, y, x' and y" being greater than 0 EO represents an ehtylene oxide group, an PrO represents a propylene oxide group.

4. A water-based crop-protection formulation composition as claimed in claim 3, wherein, in said compound of formula I, $R^1$ is hydrogen, $(C_1-C_{24})$-alkanoyl which is optionally substituted and/or optionally unsaturated, $(C_1-C_{24})$-alkyl which is optionally substituted and/or optionally unsaturated, $(C_6-C_{12})$-aryl which is optionally substituted, and $R^2$ is a basic amino acid.

5. A water-based crop-protection formulation composition as claimed in claim 3, wherein, in said compound of formula I, $R^1$ is hydrogen, $(C_1-C_{24})$-alkyl, ricinoleyl or phenyl which is substituted with 1, 2, or 3 identical or different $(C_1-C_{16})$-alkyl or $(C_6-C_{12})$-aryl radicals.

6. A water-based crop-protection formulation composition as claimed in claim 3, wherein, in said compound of formula I, $R^1$ is hydrogen $(C_1-C_{24})$-alkyl, ricinoleyl or mono, di- or tri-$(C_1-C_{16})$-alkylphenyl or mono-, di- or tri-$(C_6-C_{22})$-arylphenyl.

7. A water-based crop-protection formulation composition as claimed in claim 3, wherein, in said compound of formula I, x' is greater than 0 if x=0.

8. A water-based crop-protection formulation composition as claimed in claim 4, wherein, in said compound of formula I, x' is greater than 0 if x=0.

9. A water-based crop-protection formulation composition as claimed in claim 5, wherein, in said compound of formula I, x' is greater than 0 if x =0.

10. A water-based crop-protection formulation composition as claimed in claim 6, wherein, in said compound of formula I, x' is greater than 0 if x=0.

* * * * *